US011517217B2

(12) United States Patent
McMichael

(10) Patent No.: US 11,517,217 B2
(45) Date of Patent: Dec. 6, 2022

(54) IN-SCALE TABLET DISPLAY FOR MEDICAL DEVICE POSITION GUIDANCE

(71) Applicant: Avent, Inc., Alpharetta, GA (US)

(72) Inventor: Donald McMichael, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 758 days.

(21) Appl. No.: 16/377,316

(22) Filed: Apr. 8, 2019

(65) Prior Publication Data

US 2020/0315494 A1    Oct. 8, 2020

(51) Int. Cl.
*A61B 5/00* (2006.01)
*A61B 5/06* (2006.01)
*A61B 34/20* (2016.01)
*A61B 34/00* (2016.01)
*A61J 15/00* (2006.01)

(52) U.S. Cl.
CPC .............. *A61B 5/062* (2013.01); *A61B 5/065* (2013.01); *A61B 5/6852* (2013.01); *A61B 5/7425* (2013.01); *A61B 34/20* (2016.02); *A61B 5/0084* (2013.01); *A61B 34/73* (2016.02); *A61B 2034/2051* (2016.02); *A61B 2034/731* (2016.02); *A61J 15/0015* (2013.01)

(58) Field of Classification Search
CPC ......... A61K 38/08; A61K 38/10; A61P 11/12; C07K 7/06; C07K 7/08; C07K 7/00; A61B 5/062; A61B 5/065; A61B 5/6852; A61B 5/7425; A61B 34/20; A61B 5/0084; A61B 34/73; A61B 2034/2051; A61B 2034/731; A61B 2090/364; A61J 15/0015
See application file for complete search history.

(56) References Cited

U.S. PATENT DOCUMENTS

| 4,836,214 | A |  | 6/1989 | Sramek |
| 4,921,481 | A |  | 5/1990 | Danis et al. |
| 6,334,064 | B1 |  | 12/2001 | Fiddian-Green |
| 6,357,447 | B1 |  | 3/2002 | Swanson et al. |
| 7,818,155 | B2 |  | 10/2010 | Stuebe et al. |
| 7,855,723 | B2 | * | 12/2010 | Preiss .................. G06K 9/6211 |
|  |  |  |  | 345/419 |
| 8,147,486 | B2 |  | 4/2012 | Honour et al. |
| 8,613,702 | B2 |  | 12/2013 | Feer et al. |
| 8,801,601 | B2 |  | 8/2014 | Prisco et al. |
| 8,986,230 | B2 |  | 3/2015 | Nishtala |
| 9,179,971 | B2 |  | 11/2015 | Kirschenman |

(Continued)

FOREIGN PATENT DOCUMENTS

| EP | 1 837 828 A2 | 9/2007 |
| WO | WO 92/17150 | 10/1992 |
| WO | WO 2006/076214 A2 | 7/2006 |

OTHER PUBLICATIONS

International Search Report and Written Opinion for PCT/US2020/026866, dated Jul. 21, 2020, 14 pages.

*Primary Examiner* — Joel Lamprecht
(74) *Attorney, Agent, or Firm* — Dority & Manning, P.A.

(57) ABSTRACT

An in-scale display device is provided. The in-scale display device includes a tablet or mobile device having an electronic display screen that is configured to display at least one reference image in-scale with a subject. A medical device position guidance system including the in-scale display device and an invasive medical device system, and a method of using the medical device position guidance system, are also provided.

21 Claims, 10 Drawing Sheets

(56) References Cited

U.S. PATENT DOCUMENTS

| | | | |
|---|---|---|---|
| 9,226,878 B2 | 1/2016 | Elia et al. | |
| 9,295,395 B2 | 3/2016 | Elia et al. | |
| 9,532,739 B2 | 1/2017 | Bennett-Guerrero | |
| 9,610,227 B2 | 4/2017 | Elia | |
| 9,642,779 B2 | 5/2017 | Elia et al. | |
| 9,713,579 B2 | 7/2017 | Elia et al. | |
| 9,918,907 B2 | 3/2018 | Kuhn | |
| 2008/0097179 A1 | 4/2008 | Russo | |
| 2008/0167607 A1 | 7/2008 | Pfeiffer et al. | |
| 2008/0249467 A1 | 10/2008 | Burnett et al. | |
| 2012/0016256 A1 | 1/2012 | Mabary et al. | |
| 2012/0277619 A1 | 11/2012 | Starkebaum et al. | |
| 2013/0144124 A1 | 6/2013 | Prisco et al. | |
| 2013/0197357 A1 | 8/2013 | Green et al. | |
| 2013/0225946 A1 | 8/2013 | Feer et al. | |
| 2014/0193056 A1* | 7/2014 | Neff | G06T 19/00 382/131 |
| 2014/0357984 A1 | 12/2014 | Wallace et al. | |
| 2015/0238388 A1 | 8/2015 | Kuhn | |
| 2015/0282734 A1 | 10/2015 | Schweikert et al. | |
| 2016/0113843 A1 | 4/2016 | Elia et al. | |
| 2016/0129223 A1 | 5/2016 | Kirschenman | |
| 2016/0331298 A1 | 11/2016 | Burnett et al. | |
| 2017/0071502 A1 | 3/2017 | Bennett-Guerrero | |
| 2017/0119329 A1 | 5/2017 | Warner et al. | |
| 2017/0202750 A1 | 7/2017 | Elia | |
| 2018/0078195 A1 | 3/2018 | Sutaria et al. | |
| 2018/0092698 A1 | 4/2018 | Chopra et al. | |
| 2018/0110440 A1 | 4/2018 | Tegg | |
| 2018/0161249 A1 | 6/2018 | Elia et al. | |
| 2018/0289536 A1 | 10/2018 | Burnett | |

* cited by examiner

IN-SCALE TABLET DISPLAY FOR MEDICAL DEVICE POSITION GUIDANCE

FIELD OF THE INVENTION

The subject matter of the present invention relates generally to medical device position guidance system having a tablet or mobile device with a display screen configured to display an in-scale reference image of an invasive medical device.

BACKGROUND

Physicians and other health care providers frequently use catheters to treat patients. The known catheters include a tube which is inserted into the human body. Certain catheters are inserted through the patient's nose or mouth for treating the gastrointestinal tract. These catheters, sometimes known as enteral catheters, typically include feeding tubes. The feeding tube lies in the stomach or intestines, and a feeding bag delivers liquid nutrient, liquid medicine or a combination of the two to the patient.

Other types of catheters are inserted into the patient's veins or arteries for treating the cardiovascular system. These intravascular catheters include, among others, the central venous catheter, peripheral venous catheter and the peripherally inserted central catheter. These catheters include a relatively small tube that passes through the patient's veins or arteries. Depending on the application, the health care providers can use these intravascular catheters to remove blood vessel blockages, place inserts into blood vessels and to provide patients with injections of medications, drugs, fluids, nutrients, or blood products over a period of time, sometimes several weeks or more.

When using these known enteral and intravascular catheters, it is important to place the end of the catheter at the proper placement within the human body. Erroneous placement of the catheter tip may injure or harm the patient. For example, if the health care provider erroneously places an enteral catheter into the patient's lungs, liquid may be introduced into the lungs with harmful results.

If the health care provider erroneously places an intravascular catheter into the wrong blood vessel of the cardiovascular system, the patient may experience infection, injury or a harmful blockage.

It is also prudent to check that the exit aperture of the feeding tube (typically located at the distal end/tip of the tube) remains in its desired location over the period of treatment, e.g., feeding. Protocols that address this requirement in enteral feeding tubes include frequent monitoring for the appropriate pH of fluids extracted from the feeding tube when not carrying nutritional liquids and careful patient monitoring to ensure nutritional uptake is as expected.

One existing catheter locating means involves using an electromagnetic coil positioned inside the catheter and an electromagnetic coil locating receiver outside of the patient's body to approximate and display the catheter position. However, these systems also have several disadvantages. For example, there can be discrepancies between the size and placement of the catheter tube shown on the display and the actual size and placement of the catheter tube. These discrepancies can lead to users misinterpreting the displayed information related to the placement of the catheter tube within the subject.

Consequently, there is a need for an in-scale display for a medical device position guidance system. In particular, an in-scale display that rests on a subject and displays the placement of a medical device in-scale with the subject would also be useful.

SUMMARY

The present invention is directed to a display device including: at least one electronic display screen having a surface area; at least one signal receiver configured to detect a signal generated by a signal generator; a processor; and a memory device. The memory device stores instructions which, when executed by the processor, cause the processor to (i) detect the signal generated by the signal generator, (ii) determine the distance between the at least one signal receiver and the signal generator, and (iii) cause the display device to display at least one reference image on the electronic display screen representing the size, position and/or orientation of the signal receiver relative to the signal generator, wherein the at least one reference image is in-scale with the signal generator.

In one particular embodiment, the at least one signal receiver can include an electromagnetic receiver having at least one wire coil, further wherein the at least one signal receiver can detect an electromagnetic field generated by the signal generator by measuring a voltage of a current induced in the at least one wire coil by the electromagnetic field.

In another embodiment, the electronic display screen can be configured to be placed within a target area over a target area of the subject. Moreover, the at least one reference image can be configured to represent the size, position and/or orientation of the signal receiver relative to the signal generator based on the location of the signal receiver within the target area relative to the signal generator. In addition, when the electronic display screen moves from a first point within the target area to a second point within the target area, the at least one reference image can move to display the location of the at least one signal receiver at the second point within the target area.

In an additional embodiment, the electronic display screen can be configured to be movable in relation to a surface of the subject's body.

In yet another embodiment, the display device can be integrated into a tablet computer or mobile device.

In still another embodiment, the electronic display screen can be configured to display movement of the signal generator in the superior/inferior and/or lateral/medial directions of the subject's body when the electronic display screen is placed over an anterior surface of the subject's body.

In a further embodiment, the electronic display screen can be configured to display movement of the signal generator in the superior/inferior and/or dorsal/ventral directions of the subject's body when the electronic display screen is placed over a lateral surface of the subject's body.

The present invention is further directed to a medical device position guidance system including an invasive medical device assembly, at least one signal generator/receiver configured to generate a signal, and a display device, the display device being positionable over a surface of a subject. The invasive medical device assembly includes a sensor configured to detect a signal generated by the at least one signal generator/receiver, and an invasive medical device configured to support the sensor, the invasive medical device having an end portion configured to be inserted into the subject. The invasive medical device assembly is operatively coupled to the display device. The display device includes: at least one electronic display screen having a screen surface area; a signal receiver configured to detect a signal by the at least one signal generator/receiver; a processor; and a memory device. The memory device stores instructions which, when executed by the processor, cause the processor to (i) detect the signal generated by the signal generator/receiver via the sensor of the medical device and the signal receiver of the display device, (ii) determine the distance between the at least one signal generator/receiver and the sensor of the medical device, (iii) determine the distance between the at least one signal generator/receiver and the signal receiver of the display device, and (iii) cause the display device to display on the at least one electronic display screen at least one reference image of the size, position and/or orientation of the sensor of the medical device in relation to the position of the at last one electronic display screen, wherein the at least one reference image is configured to be in-scale with the subject's body.

In one particular embodiment, the at least one signal generator/receiver can include three signal generator/receivers configured to triangulate a shape and size of the subject's anatomy.

In another embodiment, the at least one sensor of the medical device can include an electromagnetic field sensor having at least one wire coil, further wherein the at least one sensor can detect a signal generated by the at least one signal generator/receiver by measuring a voltage of a current induced in the at least one wire coil by the electromagnetic field.

In an additional embodiment, the electronic display screen can be configured to be placed over a target area of the subject. Moreover, the display device can display the at least one reference image when the sensor of the medical device is positioned beneath the screen surface area when the electronic display screen is placed over the target area of the subject.

In yet another embodiment, the electronic display screen can be configured to be movable in relation to a surface of the subject's body.

In still another embodiment, when the electronic display screen moves in relation to a surface of the subject's body, the at least one reference image can change to display the location of the at least one sensor of the medical device beneath the moved surface area of the at least one electronic display screen.

In one more embodiment, the display device can be integrated into a tablet computer.

The present invention is further directed to a method of guiding the positioning of an invasive medical device. The method includes the steps of: providing a medical device position guidance system, inserting the invasive medical device into the subject's body, positioning the screen surface area of the display device over a target area of the subject's body in a predetermined arrangement such that the at least one signal receiver of the display device is in a predetermined position, determining the position of the at least one sensor of the medical device with respect to the at least one signal generator/receiver, determining the position of the at least one signal receiver of the display device with respect to the at least one signal generator/receiver, and displaying the position of the at least one sensor of the medical device on the at least one electronic display screen when the at least one sensor of the medical device is positioned within the target area of the subject's body.

In one particular embodiment, the method can further include a step of positioning the at least one signal generator/receiver on a surface of the subject. Moreover, the method can include a step of placing the display device over a surface of the subject after the step of positioning the at least one signal generator/receiver on a surface of the subject.

In another embodiment, the method can include a step of moving the screen surface area of the display device in relation to the subject, wherein the at least one reference image changes to display the location of the at least one sensor of the medical device below the screen surface area of the at least one electronic display screen as the at least one electronic display screen moves.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
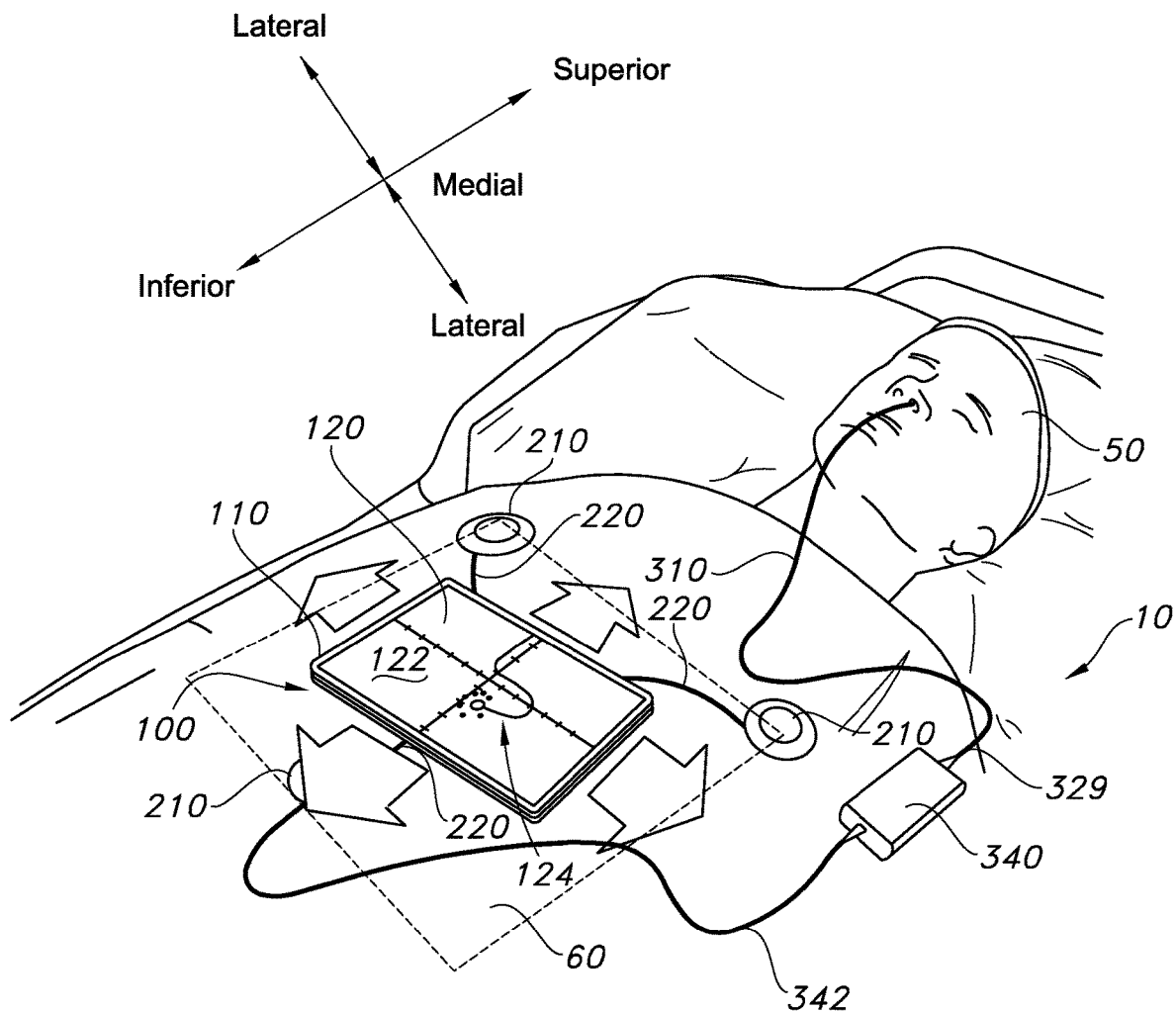
FIG. 1 illustrates a perspective view of an in-scale display device used in a medical device position guidance system according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

As used herein, the term "in-scale" indicates an article or image that is in proportion to its surroundings, with all parts the right size in relation to each other.

Generally speaking, the present invention is directed to a display device for a medical device position guidance system. The display device includes at least one electronic display screen having a surface area; at least one signal receiver configured to detect a signal generated by a signal generator; a processor; and a memory device storing instructions. When the instructions stored by the memory are executed by the processor, they cause the processor to (i) detect the signal generated by the signal generator, (ii) determine the distance between the at least one signal receiver and the signal generator, and (iii) cause the display device to display at least one reference image on the electronic display screen representing the size, position and/or orientation of the signal receiver relative to the signal generator. A medical device position guidance system including the display device and a method for the use of the system during placement of a medical device inside a body are also provided. The at least one reference image is in-scale with the signal generator. Because of the specific components of the display device, medical device position guidance system, and their methods of use, the present inventor has found that the placement of a medical device within a subject's body can be more accurately graphically represented in-scale with the anatomy of the body to improve the ease of placement of the medical device.

The specific features of the in-scale display device and medical device position guidance system of the present invention may be better understood with reference to FIGS. 1-10.

Figure 3:
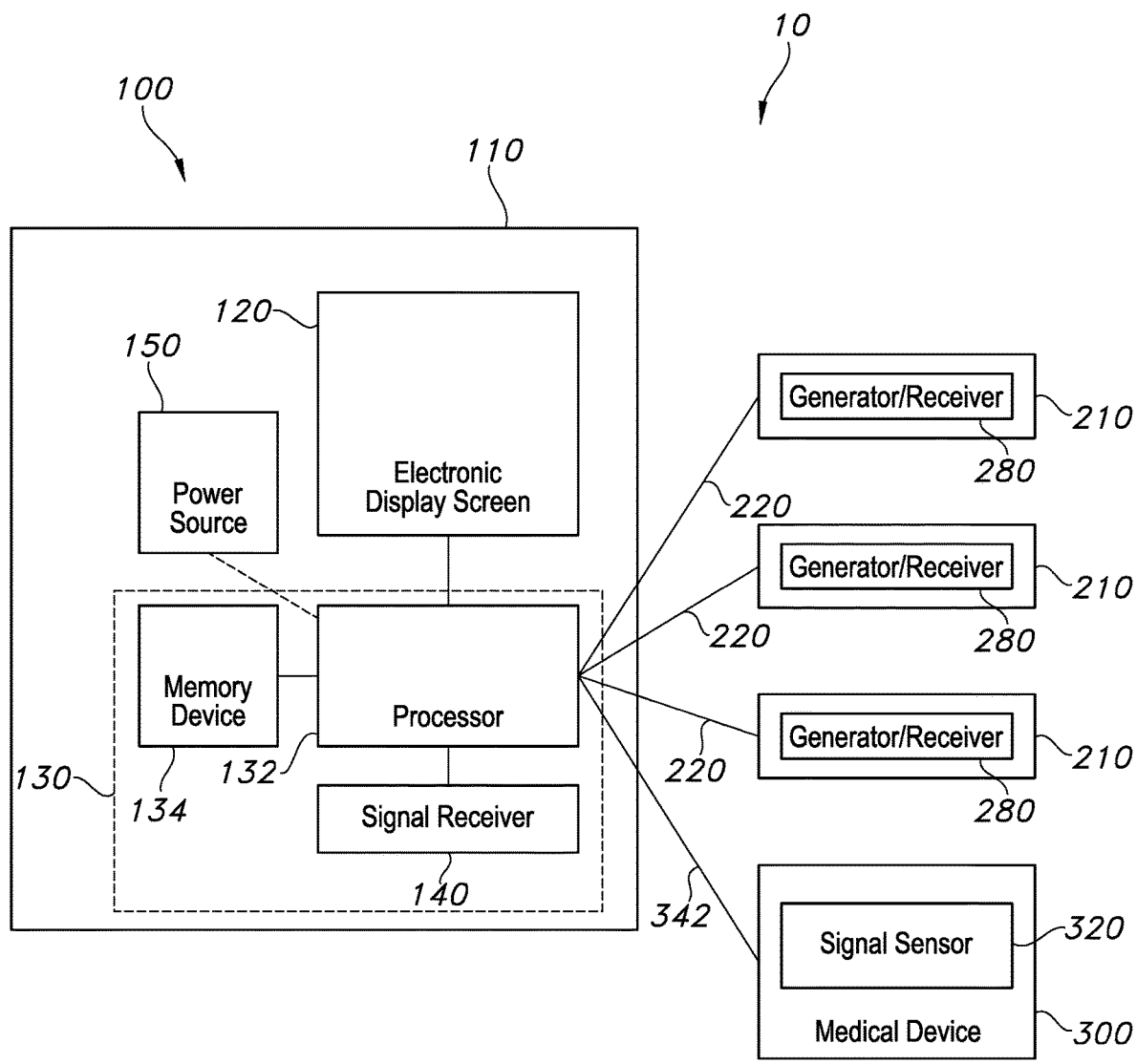
FIG. 3 illustrates a block diagram of a medical device position guidance system according to one particular embodiment of the present invention.

Referring now to FIG. 1, one embodiment of an in-scale display device 100 used in conjunction with a medical device position guidance system 10 is shown. The in-scale display device 100 includes a tablet computer 110 or other mobile device having an electronic display screen 120. The electronic display screen 120 has a screen surface area 122. The screen surface area 122 can be at least a portion of a top surface of the tablet computer 110. For example, as shown in FIG. 1, the screen surface area 122 can be substantially the entire top surface of the tablet computer 110. As shown in FIG. 3, the tablet computer 110 of the in-scale display device 100 can additionally include a control unit 130 having a processor 132 and a memory device 134. The tablet computer 110 additionally has a power source 150. The power source 150 can be a battery 152 within the tablet computer 110, or the power source 150 can be an external power source configured to connect to the tablet computer 110 by a wired or wireless connection.

The electronic display screen 120 of the in-scale display device 100 can be a light emitting diode display (LED), liquid crystal display (LCD), plasma display, or any other suitable display mechanism. For example, the electronic display screen 120 can be curved to fit the anatomical shape of an intended surface of the patient's body, such as the top surface of the abdomen as shown in FIG. 1. In another embodiment, the electronic display screen 120 can be flexible to conform to the anatomical shape of the subject's body 50.

The in-scale display device 100 additional includes a signal receiver 140 (e.g., an electromagnetic receiver), which can be part of the control unit 130. The signal receiver 140 is configured to detect a signal (e.g., a magnetic field) generated by a signal generator. For example, the signal receiver 140 can be an electromagnetic receiver in the form of one or more coils of wire(s). The coil(s) are operable to receive an induced current in response to a magnetic field generated by a signal generator in the form of an electromagnetic field generator when the magnetic field is directed toward and reaches the coil(s). It should be appreciated that the coil(s) of the electromagnetic receiver 140 can be any suitable structure or structures capable of receiving a current in response to a generated magnetic field. The signal receiver 140 is in communication with the processor 132 of the display device 100 to send information regarding the position and orientation of the signal generator relative to the signal receiver 140. The information regarding the position and orientation of the signal generator relative to the electromagnetic receiver 140 can be obtained by sensing the voltage of the induced current in the coil(s) and obtaining the drive signals used to create the magnetic field by the signal generator, to assess the distance between the receiver 140 and the generator. In another embodiment, the signal receiver 140 can detect the strength of a signal on a defined frequency that is generated by a signal generator. The strength of the detected signal on the defined frequency can be used to determine the distance between the signal receiver 140 and the signal generator.

The memory device 134 can store image processing algorithms which, when executed by the processor 132, cause the processor 132 to generate at least one reference image 124 on the electronic display screen 120 relating to the position and orientation of the signal generator relative to the receiver 140. The at least one reference image 124 can be displayed in-scale with the anatomy of the subject 50. For example, the at least one reference image 124 can display anatomical landmarks of the subject's internal or external anatomy, such as the xiphoid process.

As shown in FIG. 3, the in-scale display device 100 can be part of a medical device position guidance system 10. In addition to the in-scale display device 100 having a processor 132 and a memory 134, the medical device position guidance system 10 can include a plurality of non-invasive external detector devices 210 electronically coupled to the processor 132 by a wire, cable, signal data connection, signal carrier or wireless connection, e.g. cable 220 shown in FIG. 1, and optionally an invasive medical device 300 in communication with the plurality of external detector devices 210 and operatively coupled to the in-scale display device 100 by a wire, cable, cord or electrical extension 342, which, in turn, is operatively coupled to the processor 132. Each of the plurality of external detector devices 210 are configured to be positioned in a distributed arrangement on a surface of a subject 10 (see, e.g., FIGS. 1-2) which is a mammal, such as a human. Although the illustrated example depicts a human, it should be appreciated that medical device position guidance system 100 could be used with any mammals such as domestic animals.

In general, and referring to FIGS. 1, 8 and 9A-B, the plurality of noninvasive external detector devices 210 each includes a housing 212 which supports a signal generator/receiver 280 operably coupled to the processor 132, where the processor 132 is coupled to a memory device 134. According to the embodiment, the medical device position guidance system 10 is operable to provide audiovisual information about the shape, size, and orientation of a subject's anatomy through a wired or wireless connection between the plurality of external detector devices 210 and the in-scale display device 100. The medical device position guidance system 10 can be further operable to provide audiovisual information about the position and orientation of the invasive medical device 300 relative to the plurality of external detector devices 210, the position of the in-scale display device 100 relative to the subject 50, and the subject's detected anatomy, through a wired or wireless connection between the plurality of external detector devices 210, the invasive medical device 300, and the in-scale display device 100.

Figure 8:
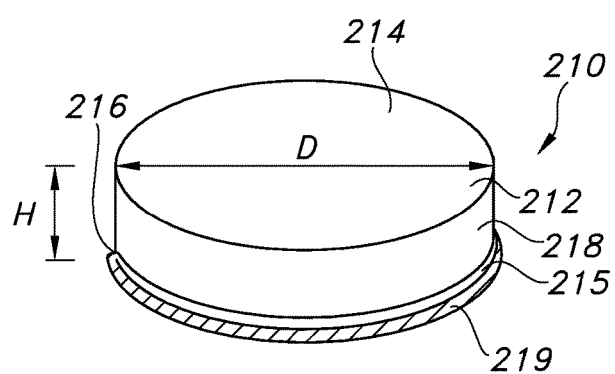
FIG. 8 illustrates a perspective view of a housing of an external detector device of the medical device position guidance system of the present invention.
Figure 9A:
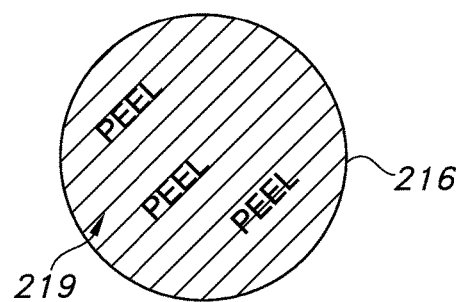
FIGS. 9A-B illustrate bottom views of the housing of FIG. 8.
Figure 9B:
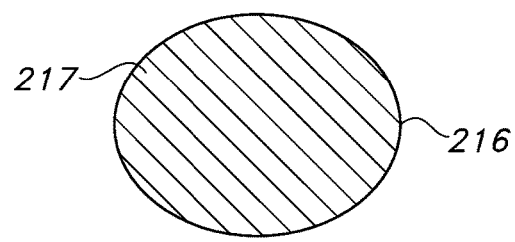

In general, and referring to FIGS. 8 and 9A-B, the plurality of noninvasive external detector devices 210 each includes a housing 212 which supports a signal generator/receiver 280 operably coupled to the processor 132, where the processor 132 is coupled to a memory device 134. According to the embodiment, the medical device position guidance system 10 is operable to provide audiovisual information about the shape, size, and orientation of a subject's anatomy through a wired or wireless connection between the plurality of external detector devices 210 and the in-scale display device 100. The medical device position guidance system 10 can be further operable to provide audiovisual information about the position and orientation of the invasive medical device 300 relative to the plurality of external detector devices 210, the position of the in-scale display device 100 relative to the subject 50, and the subject's detected anatomy, through a wired or wireless connection between the plurality of external detector devices 210, the invasive medical device 200, and the in-scale display device 100.

As illustrated in FIGS. 8 and 9A-B, each of the external detector devices 210 includes a housing 212 surrounding a signal generator and/or receiver 280. The housing 212 can include an upper surface 214, a lower surface 216, and at least one side surface 218 extending from the upper surface to the lower surface. For example, as shown in FIG. 9A, the upper surface 214 and the lower surface 216 can be circular or oval in shape and have a continuous side surface 218 extending therebetween, forming a generally cylindrical-shaped housing 212. In another embodiment (not shown), the upper surface 214 and the lower surface 216 can be rectangular in shape and can have four side surfaces 218 extending therebetween corresponding to each of the sides of the rectangle. However, the external shape of the housing 212 of each external detector device 210 is of little consequence to the way in which the actual signal generator and/or receiver 280 works. As such, the housing 212 can have any other suitable external shape based on a particular application of the medical device position guidance system 100.

The housing 212 of each external detector device 110 can have a footprint (i.e., shape and size of the lower surface 216) that is generally comparable to standard electrocardiogram leads. For example, the housing 212 can have a diameter D extending across the widest portion of the upper surface 214 or lower surface 116 that is in a range from about 0.5 inches (1.25 cm) to about 5 inches (13 cm), or any value or range therebetween, such as from about 1 inch (2.5 cm) to about 3 inches (7.6 cm), for example from about 1.5 inches (3.8 cm) to about 2.5 inches (6.4 cm). The at least one side surface 218 of the housing 212 can have a height H in a range from about 0.25 inches (0.63 cm) to about 2 inches (5.1 cm), or any value or range therebetween, such as from 0.3 inches (0.76 cm) to about 1 inch (2.5 cm), for example about 0.5 inches (1.25 cm). In addition, each of the external detector devices 210 can be lightweight.

As shown in FIGS. 8 and 9A-B, each external detector device 210 can further include a fixation mechanism 215 that is configured to affix the external detector device 210 to the subject. In a preferred embodiment, the external detector device 210 can be directly affixed to the subject's body 10 by the fixation mechanism 215 so that the external detector device 210 maintains a fixed reference point in relation to the subject 50. Thus, when the subject 50 moves, the external detector device 210 moves with the subject 50 to maintain a static frame of reference with respect to the particular patient. The fixation mechanism 215 can be positioned on the lower surface 216 of the external detector device housing 212. For example, the fixation mechanism 215 can include an adhesive material 217 that is configured to affix the external detector device 210 to the skin of the subject, a patch on the subject's body, or a garment worn by the subject. The adhesive material 217 can be an adhesive substrate that can be adhesive on both sides such that it adheres to the lower surface 216 of the housing 212 on one side and to a subject's body or garment on the other side. When the fixation mechanism 215 is adhesive material 217 adhered to the lower surface 218 of the housing 212, the external detector device 210 can additionally include a peelable protective sheet 219 covering the entire adhesive material 217. The peelable protective sheet 219 can be removed prior to affixing the adhesive 217 to the subject 50 or the subject's garment. Optionally, a used adhesive substrate 217 can be removed from the housing 212 and discarded, and a new adhesive substrate 217 can be applied. Alternatively, the adhesive material 217 can be any suitable adhesive arrangement which is capable of releasably adhering the housing 212 to the subject's skin or garment. In other embodiments, the fixation mechanism 215 can include a clip, pin, magnet, hook and loop system, or any other suitable means for affixing the external detector device 210 to a subject's body or garment. By using a fixation mechanism 215 on each external detector device 210 that can affix the external detector device 210 to the subject's body or garment, the frame of reference of each external detector device 210 can remain stationary with the subject's body. Thus, the likelihood of positional errors when using the medical device position guidance system 100 can be reduced as compared to other guidance systems because there can be fewer complications arising due to movement of the subject's body.

As shown in FIGS. 1 and 2A-C, the plurality of external detector devices 210 are configured to be positioned on the external anatomy of a subject 50 in a predetermined arrangement. The predetermined arrangement of the external detector devices 210 can be specific to a particular medical device being positioned in the subject 50. The predetermined arrangement can include multiple predetermined external fixation points on the subject's external anatomy, where each of the predetermined external fixation points are distributed or separated from each other as shown in FIGS. 1 and 2A-C. The predetermined external fixation points can be based on well-known external anatomical landmarks. In some embodiments, the well-known external anatomical landmarks can be bony landmarks, as the bony landmarks can be located visually or palpated on subjects of any shape or size regardless of physical presentation of the subject, such as the presence of adipose tissue, edema, or other tissues. Having the external detector devices 210 positioned on known anatomical landmarks on the subject's body 50 provides a known anatomical frame of reference which can enable anthropometric data to be applied in order to approximate three-dimensional locations and sizes of internal anatomical structures.

Figure 10:
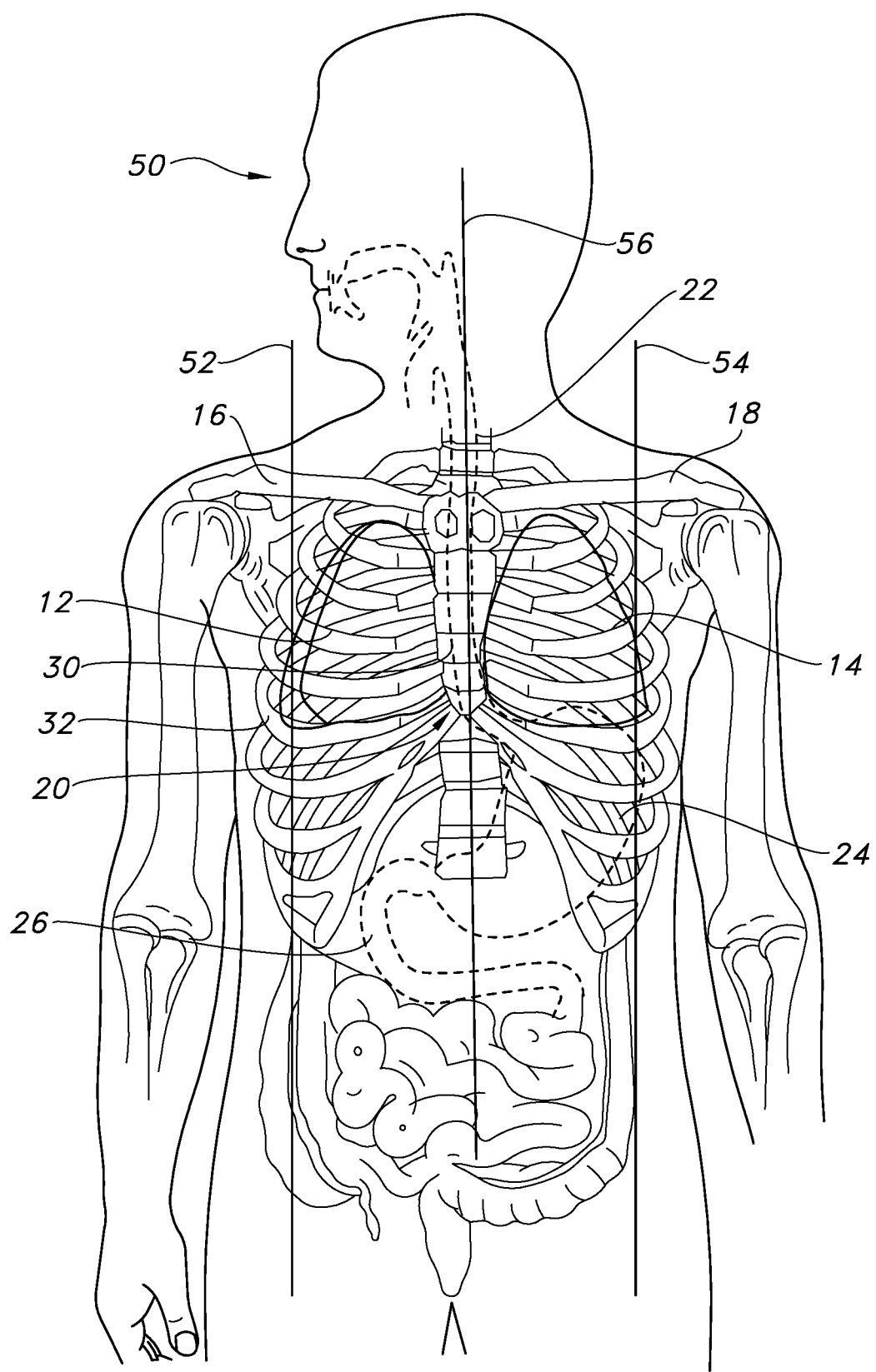
FIG. 10 illustrates anatomical landmarks of a human body.
Figure 11:
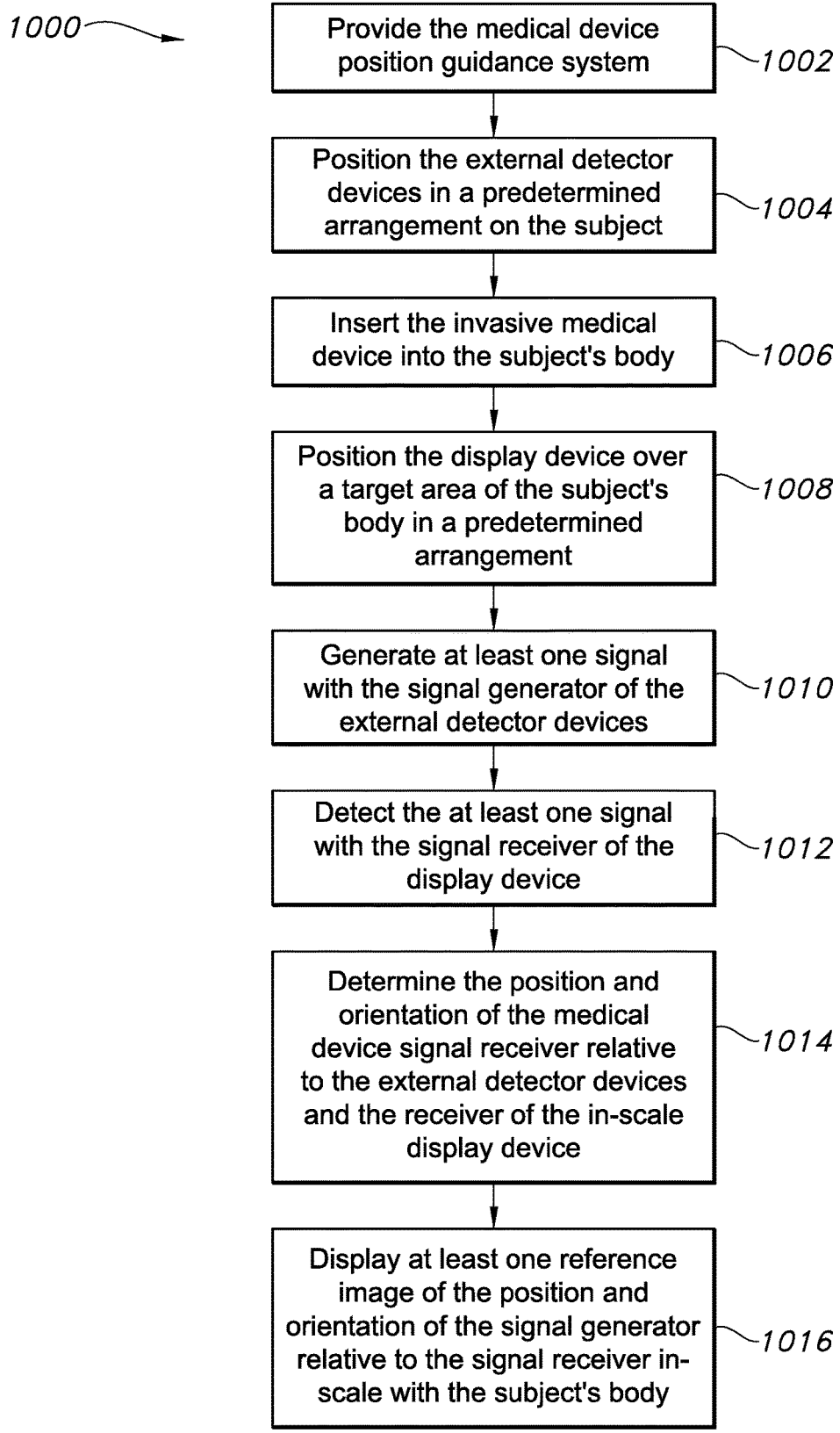
FIG. 11 illustrates a method of using the medical device position guidance system of FIG. 3.

For example, as illustrated in FIGS. 1 and 2A-C, when the medical device position guidance system 100 is used to determine a subject's upper anatomy such as for inserting an enteral catheter (feeding tube), three external detector devices 210 can be positioned on the subject 50. For instance, one device 210 can be placed at a right upper landmark, such as the right midclavicular line 52, one device 210 can be placed at a left upper landmark, such as the left midclavicular line 54, and one device 210 can be placed at a central landmark, such as the xiphoid process 20. As illustrated in FIG. 10, the xiphoid process 20 is the cartilaginous section at the lower end of the sternum 30 which is generally positioned along the mid-sagittal line 50 and which is not attached to any ribs 32 and is gradually ossified in adult humans. The right and left midclavicular lines 52 and 54 are each imaginary lines which are generally parallel to the mid-sagittal line 50 and pass downwards over the trunk of the human body 10 through the midpoint of the right and left clavicle bones 16 and 18, respectively. However, the midclavicular lines 52 and 54 and the xyphoid process 20 are not the only landmarks that could be used for this purpose. There may be other points of the body to which the predetermined arrangement of the plurality of external detector devices 210 could be reliably co-located or located with a predetermined offset for use in a reliable position guidance system.

Figure 4:
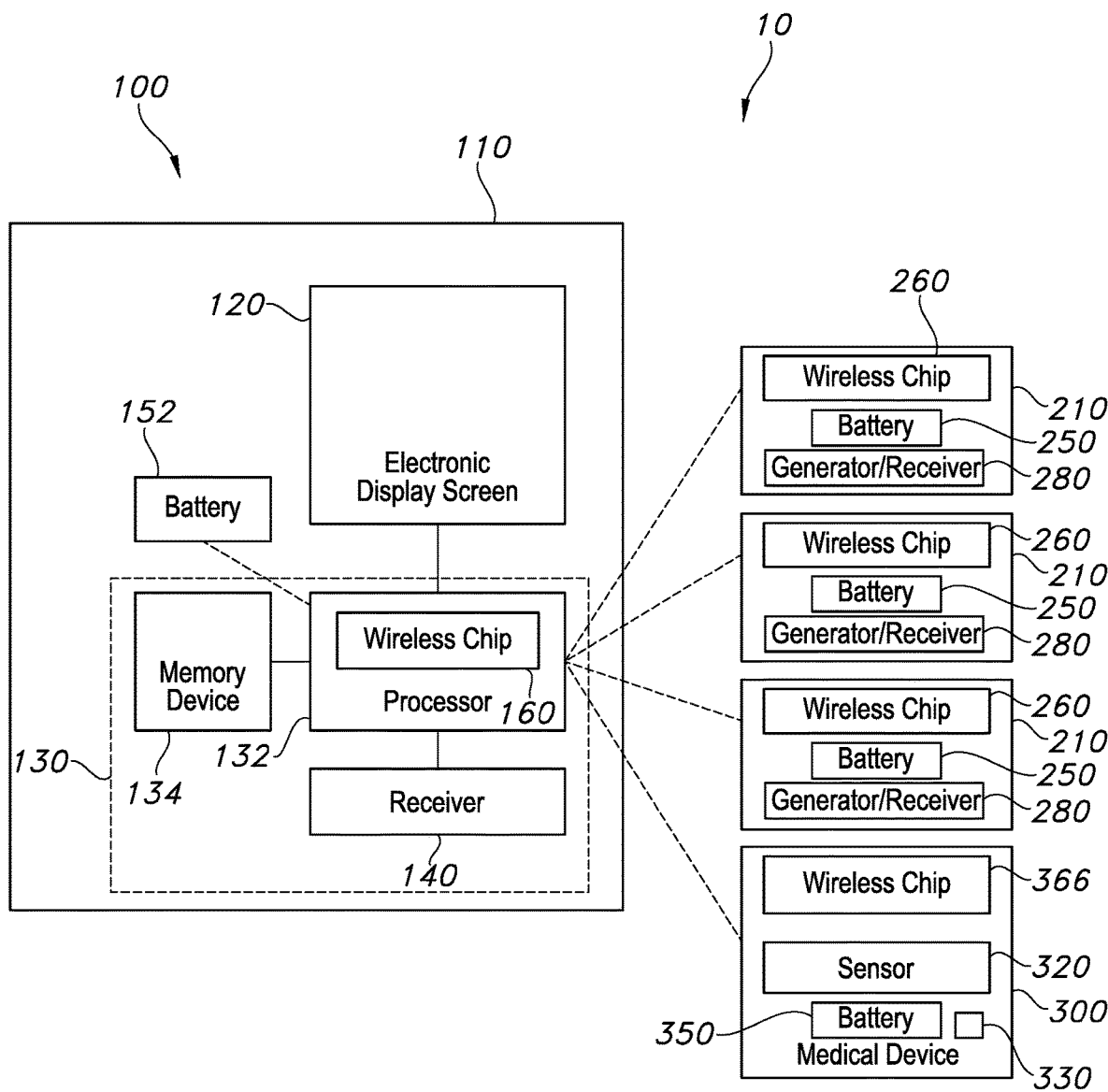
FIG. 4 illustrates a block diagram of a medical device position guidance system according to an alternative embodiment of the present invention.

As illustrated in FIGS. 3-4, each external detector device 210 includes a signal generator and/or receiver 280. In one embodiment, each external detector device may include an electromagnetic field generator formed through a plurality of coils of wire(s). The signal generator and/or receiver can receive electrical energy through a wired connection to power supply 150, as shown in FIG. 3, or can be a battery 250 within the external detector device 210 as shown in FIG. 4. When the power source sends electrical current to the signal generator 80, the signal generator 280 can transmit a signal or electromagnetic field capable of being detected by an electromagnetic receiver. Although coils are disclosed as one example of a signal generator, it should be appreciated that the signal generator can include any suitable mechanism or device which generates or produces a detectable signal such as radiofrequency generation, magnetic energy or a magnetic field, such as a permanent magnet, resistive magnet, or superconducting magnet. The signal generator/receiver 280 of each external detector device 210 can additionally or alternatively include a signal receiver that can detect an electromagnetic field or signal generated by a signal generator, such as the signal generators of the other external detector devices 210. The signal receivers can each include at least one receiver coil, such as three receiver coils, that are operable to receive an induced current and detect the induced voltage in response to a magnetic field generated by a signal generator when a signal, such as a magnetic field or defined frequency, is directed toward and reaches the receiver coil(s). It should be appreciated that the receiver may be any suitable structure capable of receiving a signal, such as an induced current in response to a generated magnetic field, or detecting the strength of a signal at a defined frequency. In some embodiments, each of the plurality of external detector devices 210 can include both signal generator and a signal receiver as part of the emitter/receiver 280. Additionally, there can be shielding within the emitter/receiver 280 to shield between the generator and the receiver. The shielding can prevent signal interference. For example, the shielding can be a barrier be made of conductive or magnetic materials.

In one embodiment, each external detector device 210 can be electrically connected to the display device 100 via a wire, cable, or other connection 220 to receive power from the display device 100 and to communicate with the processor 132. Alternatively, each external detector device 210 can have a wireless configuration including a battery 250 that provides a voltage to the signal generator/receiver 280 and a wireless communication chip 260 configured to communicate with the processor 132. Optionally, the wireless communication chip 260 can include a processor (not shown). The wireless communication chip 260 can be any suitable form of wireless communication capable of sending and receiving digital signals from the processor 132 of the display device 100.

When the plurality of external detector devices 210 are positioned in the predetermined arrangement on the subject 50 based on predetermined external landmarks, the locations of the landmarks can provide adequate separation of the external detector devices 210 on the subject to enable each of the external detector devices 210 to interrogate each other, i.e., for the signal generators to generate a signal and for the signal receivers to detect the signals generated by the respective signal generators of the other external detector devices 210.

As shown in FIG. 1, the plurality of external detector devices 210 are configured to be positioned on the external anatomy of a subject 50 in a predetermined arrangement. The predetermined arrangement of the external detector devices 210 can be specific to a particular medical device being positioned in the subject 50. The predetermined arrangement can include multiple predetermined external fixation points on the subject's external anatomy, where each of the predetermined external fixation points are distributed or separated from each other as shown in FIG. 1. The predetermined external fixation points can be based on well-known external anatomical landmarks. The well-known external anatomical landmarks can be bony landmarks, as the bony landmarks can be located visually or palpated on subjects of any shape or size regardless of physical presentation of the subject, such as the presence of adipose tissue, edema, or other tissues.

For example, as illustrated in FIG. 1, when the medical device position guidance system 10 is used to determine a subject's upper anatomy such as for inserting an enteral catheter (feeding tube), three external detector devices 210 can be positioned on the subject 50. For instance, in one predetermined arrangement, one device 210 can be placed at the right midclavicular line, one device 210 can be placed at the left midclavicular line, and one device 210 can be placed at the xiphoid process 20. As illustrated in FIG. 10, the xiphoid process 20 is the cartilaginous section at the lower end of the sternum 30 which is generally positioned along the mid-sagittal line 56 and which is not attached to any ribs and is gradually ossified in adult humans. The right and left midclavicular lines 52 and 54 are each imaginary lines which are generally parallel to the mid-sagittal line 56 and pass downwards over the trunk of the human body 10 through the midpoint of the right and left clavicle bones 16 and 18, respectively. However, the midclavicular lines 52 and 54 and the xyphoid process 20 are not the only bony landmarks that could be used for this purpose. There may be other points of the body to which the predetermined arrangement of the plurality of external detector devices 210 could be reliably co-located or located with a predetermined offset for use in a reliable position guidance system.

In one embodiment, as shown in FIGS. 1-2, each external detector device 210 can be electrically connected to the in-scale display device 100 via a wire, cable, or other connection 220 to receive power from the power supply of the display device 100 and to communicate with the processor. Alternatively, each external detector device 210 can have a wireless configuration including a battery that provides a voltage to the signal generator/receiver and a wireless communication chip configured to communicate with the processor 132. The wireless communication chip 360 of each external detector device 310 can be any suitable form of wireless communication capable of sending and receiving digital signals from the processor 132 of the in-scale display 100.

When the plurality of external detector devices 210 are positioned in the predetermined arrangement on the subject 50 based on predetermined external landmarks, the locations of the landmarks can provide adequate separation of the external detector devices 210 on the subject to enable the signal generators and receivers of each external detector device 210 to interrogate each other, e.g., for the generators to emit an electromagnetic field and for the receivers detect the magnetic fields emitted by the respective emitters of the other external detector devices 210. Each external detector device 210 sends signals to the processor 132 detailing the detected voltage of the induced current in the coil and also the drive signals used to generate the electromagnetic fields with the generators 280. The processor 132 compares each of the detected coil voltages and the drive signals used to create the electromagnetic fields to assess and calculate the distance and the relative angular orientation between each of receivers of the external detector devices 210 to define an electromagnetic three-dimensional volume. Using algorithms stored in the memory 134, the processor 132 uses the data collected about the electromagnetic three-dimensional volume to derive the subject's external and internal anatomical shape and size within the three-dimensional volume. For example, the memory 134 can store information related to pre-defined anthropometric relationships between the external anatomy of a subject and the corresponding internal anatomical shape and size. Thus, the anthropometric data can be applied to the detected target volume of the For example, as shown in the embodiment illustrated in FIGS. 1-2, the medical device position guidance system 10 can include three external detector devices 210 configured to triangulate and define the subject's upper external anatomy shape and size within the three-dimensional volume. This embodiment including three external detector devices 210 can be beneficial because each of the three external detector devices 310 positioned on known anatomical landmarks can form one of three points in space in order to define a single X-Y plane. The determination of an X-Y plane can allow the determination of a distance or depth in the Z-direction. Thus, using three external detector devices 310 can enable the determination of the three-dimensional volume by using the external frame of reference of the three external detector devices 310 and apply known pre-defined anthropometric relationships in order to approximate the three-dimensional locations and sizes of internal anatomical structures. The three-dimensional volume between the external detector devices 210 can define a target area 60 of the subject's body.

The memory 134 stores algorithms defining a generally known relationship between external anatomy and the internal anatomy, e.g. organs within a subject's body. The processor 132 can execute these algorithms to relate the subject's external anatomy, as detected by the external detector devices 210, to approximate the shape and size of the internal organs associated with that external anatomy. In the embodiment illustrated in FIG. 1, the upper external anatomy shape and size can be used to calculate the shape and size of the lungs, esophagus and stomach. The memory 134 can further store image processing algorithms which the processor 132 can execute in order to visually render a graphical representation, e.g. a reference image 124, of the shapes of the lungs, esophagus and stomach in approximate size and location within the three-dimensional volume and depict the rendered graphical representation or reference image 124 of the internal anatomy to scale on the electronic display screen 120 of the in-scale display 100, e.g. as illustrated in FIGS. 1-2, when the electronic display screen 120 is positioned over the subject's body 50 within the target area 60. The reference image 124 can be in-scale with the subject's anatomy, i.e., in the same size and proportion to the subject's anatomy, with all parts the right size in relation to the patient's body 50. As such, a user such as a health care provider can easily visualize the actual size and shape of the subject's internal anatomy within the target area 60 in real time and space as displayed by the reference image 124. Thus, the medical device position guidance system 10 can render a graphical representation, in the form of at least one reference image 124, of the subject's internal anatomy prior to insertion of the invasive medical device 310 to enable the accurate placement of the invasive medical device 310 in the proper location within the body.

Figure 5:
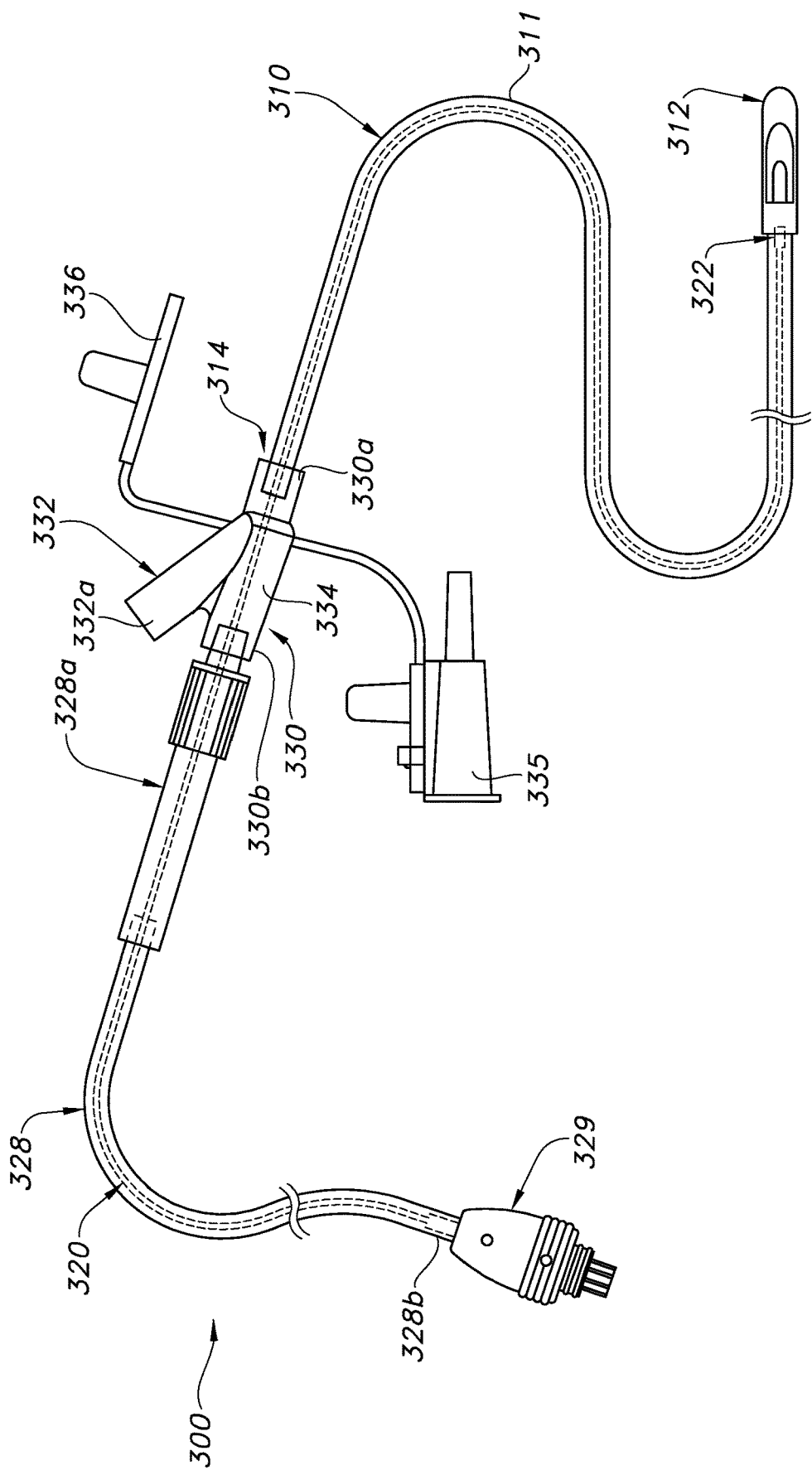
FIG. 5 illustrates a perspective view of an invasive medical device assembly of the medical device position guidance system of FIG. 3.

As shown in FIGS. 3-4, the medical device position guidance system 10 can also include an invasive medical device assembly 300, shown in FIG. 5, having an invasive medical device 310 and a signal sensor or generator system 320. The invasive medical device assembly 300 can be operatively connected to the display device 100 by a wired connection, shown in FIG. 3, or a wireless connection, shown in FIG. 4. The signal sensor or generator system 320 is configured to be disposed within the invasive medical device 310 such that the signal sensor or generator system 320 can be used to detect a position and/or orientation of the invasive medical device 310 within the subject's body.

The invasive medical device 310 can be a catheter, such as an enteral feeding tube 310 as shown in FIGS. 1 and 5. The enteral feeding tube 310 extends from a distal end 312 to a proximal end 314 and can be connected to a distal end 330a of a connector 330 at the proximal end 314. The invasive medical device assembly 300 can additionally include a tubing assembly 328 configured to house at least a portion of the electromagnetic field sensor or generator system 320. A distal end 328a of the tubing assembly 328 can connect to a proximal end 330b of the connector 330. For example, as shown in FIG. 5, the distal end 330a and proximal end 330b of the connector 330 can extend along a longitudinal axis with a lumen 334 extending therebetween. Both the distal end 330a and proximal end 330b of the connector 330 can contain openings in communication with the lumen 334 and configured to receive the feeding tube 310 and the tubing assembly 328, respectively. Optionally, the connector 330 can also include a cap or cover 335 configured to close the opening at the proximal end 330b of the connector 330. In addition, the connector 330 can include a Y-port 332 in communication with the lumen 334 and the opening at the distal end 330a. The Y-port 332 can additionally have a cap or cover 336 configured to close the opening at the proximal end 332a of the Y-port 332. The Y-port 332 can be configured to receive tubing or other suitable means for delivering enteral feeding fluid, medicine, or other fluids through the feeding tube 310.

Figure 6:
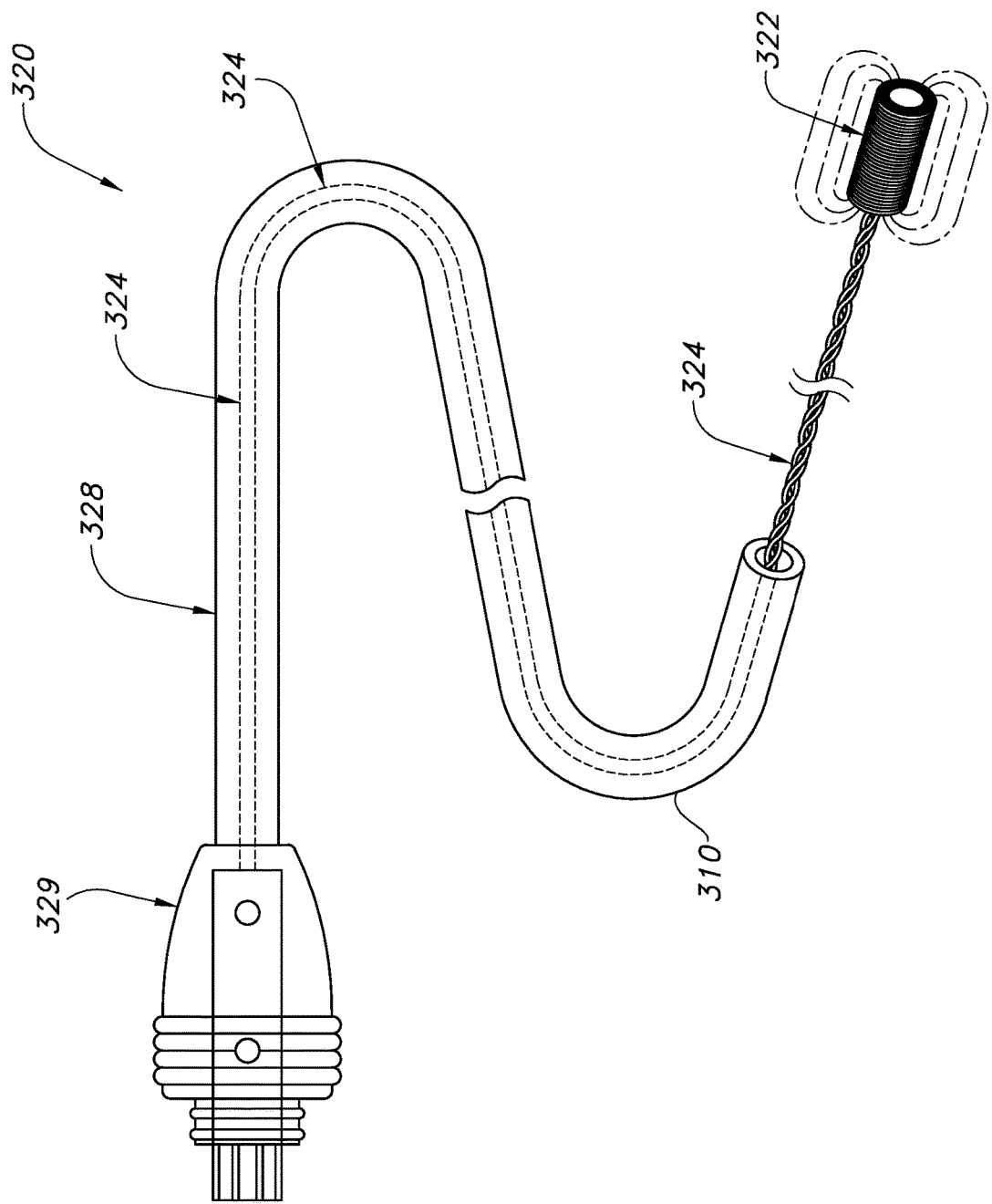
FIG. 6 illustrates a perspective view an electromagnetic field sensor or generator system of the invasive medical device assembly of FIG. 5.
Figure 7:
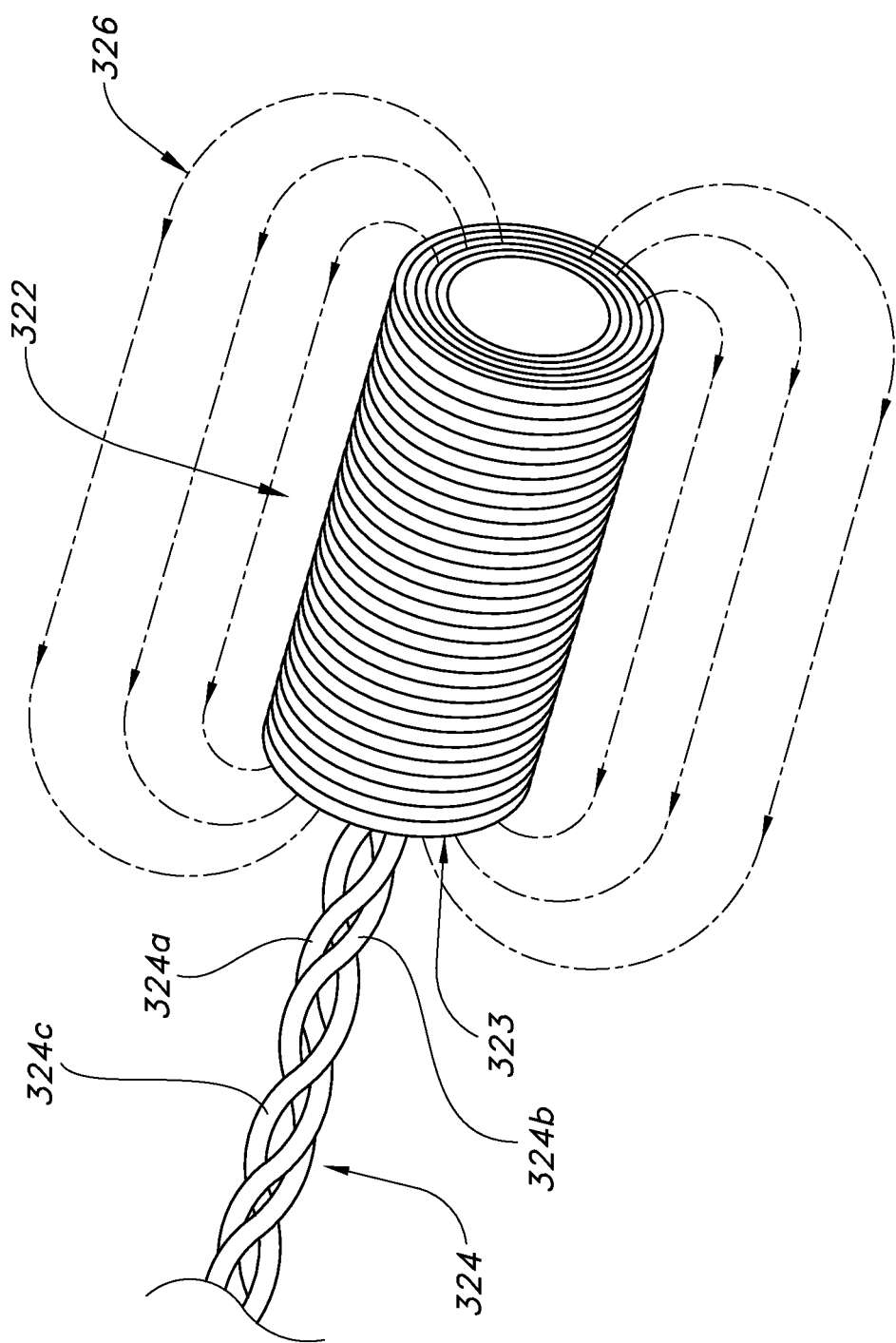
FIG. 7 illustrates an electromagnetic field sensor or generator of the embodiment of FIG. 6.

The signal sensor or generator system 320 can be in the form of an electromagnetic field sensor and generator system, as shown in FIGS. 6-7, including a wire assembly 324 comprised of one or more electrical wires, for example two wires 324a and 324b as shown in FIG. 7. The electrical wires 324a and 324b can be made of copper or any other suitable electrically conductive material. The wires 324a and 324b can be twisted around each other along the length of the wire assembly 324. In one embodiment, as shown in FIG. 7, the wire assembly 324 can additionally include an elongated stiffener 324c twisted with the wires 324a and 324b to increase the rigidity of the wire assembly 324. The elongated stiffener 324c can be made of steel or any other suitable material. The twisted configuration of the wire assembly 324 can reduce any electromagnetic field surrounding the wires 324a and 324b along the twisted length of the wire assembly 324. This reduction is caused by the counteraction of the electromagnetic forces of the electrical wires 324a and 324b. Accordingly, the signal receiver 140 receives less, if any, signal interference from any electromagnetic fields generated by the wire assembly 224.

As shown in FIG. 5, at a proximal end of the wire assembly 324, the electromagnetic field sensor or generator system 320 can include a connector 329. The connector 329 can operatively connect the system 320 to the control unit 130 of the display device 100. In one embodiment, the connector 329 can electrically connect the system 320 to the power source 150 of the display device 100. In another embodiment, the system 320 can include its own power source such as a battery 350. Alternatively, as shown in FIG. 1, the connector 329 can connect the wire assembly 324 to a connector unit 340. The connector unit 340 can have a cable 342 that operatively connects the invasive medical device assembly 300 to the control unit 130 of the in-scale display device 100.

In an embodiment of the invasive medical device assembly 300 that is in wireless communication with the display device 100, as shown in FIG. 4, the connector 329 can house a wireless chip 366 that is configured to communicate with a wireless chip 160 of the display device 100. In this embodiment, the invasive medical device assembly 300 can additionally include a control unit 360 including a memory 364 and a processor 362 to generate at least one drive signal for generating the electromagnetic field and transmitting a signal containing information about the at least one drive signal to the processor 132 of the display device 100.

As shown in FIGS. 6-7, at a distal end of the wire assembly 324, the wires form a coil configuration 322 forming coils thereby producing a magnetic field generator as described below. The coil 322 is formed from a plurality of spirals produced by wrapping a portion of the wires 324a and 324b around each other. As an electrical current is transmitted through the wires 324a and 324b, the current travels in a circular path defined by the coils. This circular motion of current produced an electromagnetic field, B field or electromagnetic radiation 326. Although the embodiment illustrated includes coils 322, it should be appreciated that the signal generator 322 can include any alternate suitable mechanism or device which generates or produces magnetic energy, a magnetic field, or any other suitable signal. In one embodiment, the magnetic field generator 322 includes a magnet such as a permanent magnet, resistive magnet or superconductive magnet.

In operation, when a power supply, e.g. power supply 150 or battery 350, sends electrical current to the coils 322, and the coils 322 transmit an electromagnetic field 326 capable of being detected by the signal receiver 140, the signal receiver 140 detects the electromagnetic field 326 generated by the magnetic field generator coils 322 inside the human body. The processor 132 causes the display device 100 to produce at least one representative image the electronic display screen 120 which can assist a healthcare provider in a feeding tube placement procedure.

In an alternative embodiment (not shown), the signal generator system 320 can be incorporated directly into the invasive medical device 310, for example, by embedding a coil 322 and/or the wire assembly 324 into a wall 311 of a catheter 310.

In yet another alternative embodiment, the signal sensor or generator system 320, e.g. an electromagnetic field sensor or generator system, can sense a signal generated by the generator/receivers 280 of the external devices 210. A coil 322 of the signal sensor or generator system 320 can receive an induced current based on its proximity to the generator/receivers 280 of each of the external devices 210. The voltage of the induced current can be transmitted via the wire assembly 324, through the connector 329 and to the processor 132 of the display device 100. Thus, the coil 322 can be capable of both sensing an electromagnetic field and generating an electromagnetic field 326 in order to determine the relative position of the invasive medical device 310 relative to the display device 100 and the external devices 210.

In use, as shown in FIGS. 1-2, the in-scale display device 100 is configured to be placed over the subject's body within the target area 60 defined by the external detector devices 210. Based on the signals sent to the processor 132, the electronic display screen 120 can display at least one reference image 124 of the subject's anatomy and/or the invasive medical device 310 within the target area 60 of the subject's body 50. Particularly, the electronic display screen 120 can display a reference image 124 of the subject's anatomy and/or the invasive medical device 310 within the target area 60 of the subject's body 50 that is directly beneath the screen surface area 122 at any given point within the target area 60. The reference image 124 can be in-scale with the subject's anatomy, i.e., in the same size and proportion to the subject's anatomy, with all parts the right size in relation to the patient's body 50. As such, a user such as a health care provider can easily visualize the actual size and shape of the invasive medical device and the subject's internal anatomy within the target area 60 in real time and space as displayed by the reference image 124.

Figure 2A:
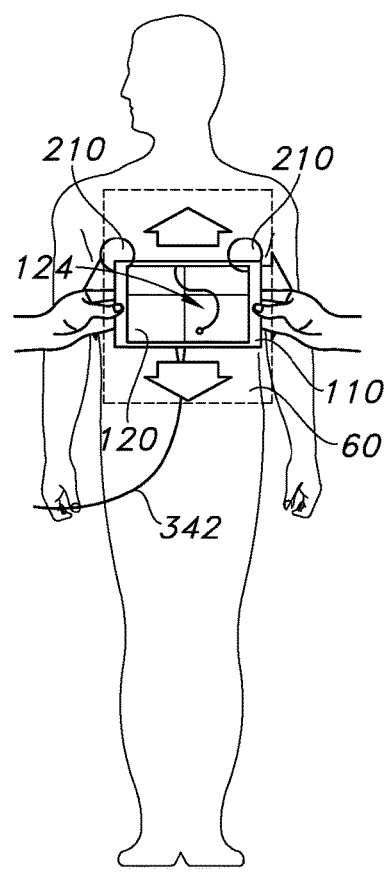
FIGS. 2A-C illustrate top views of the in-scale display device of FIG. 1 in various positions in relation to a subject.
Figure 2B:
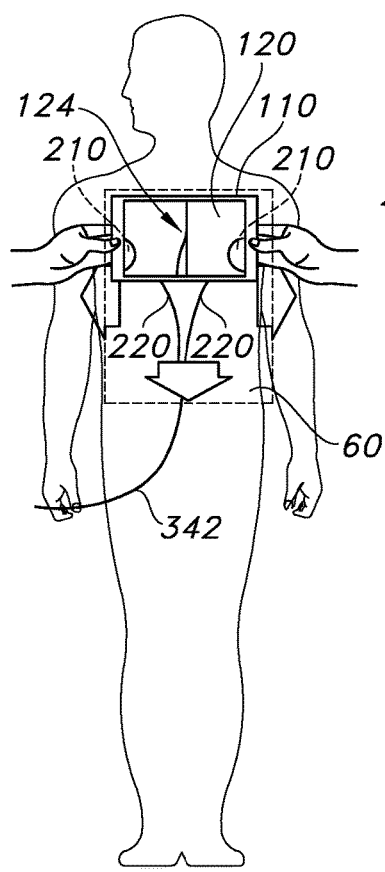
Figure 2C:
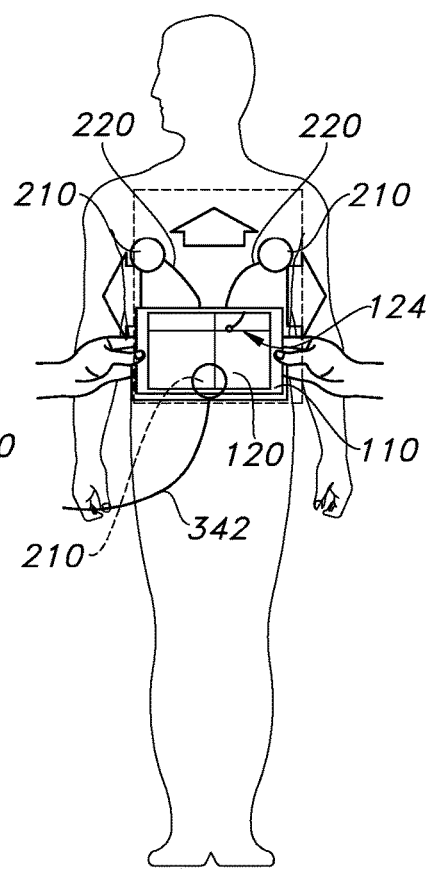

When the in-scale display 100 is moved within the target area 60, e.g. from a centered position within the target area 60 as shown in FIG. 2A to a superior position within the target area 60 as shown in FIG. 2B, the at least one reference image changes from depicting the anatomy and/or medical device beneath the centered position to the anatomy and/or medical device below the superior position. Similarly, when the in-scale display 100 is moved within the target area 60, e.g. from a superior position within the target area 60 as shown in FIG. 2B to an inferior position within the target area 60 as shown in FIG. 2C, the at least one reference image changes from depicting the anatomy and/or medical device below the superior position to the anatomy and/or medical device below the inferior position.

Thus, the in-scale display device 100 can effectively scan the subject's anatomy and/or position of the invasive medical device 310 within the target area 60 and display the subject's anatomy and/or position of the invasive medical device 310 within the target area 60 relative to the position of the screen surface area 122 of the in-scale display 100 within the target area 60.

The at least one reference image 124 displayed on the electronic display screen 120 is configured to be in-scale relative to the size of the tablet 110 and the subject's anatomy. The scale of the at least one reference image 124 is determined by triangulating the size and shape of the subject's anatomy using the external devices 210 and the algorithms stored by the memory and executed by the processor, as explained above.

The in-scale display device 100 and medical device position guidance system 10 can also be used in a method for guiding the placement of an invasive medical device, e.g., enteral feeding tube 310. The method 1000 includes a first step 1002 of providing the medical device position guidance system 10 as described above, e.g., the system 10 as illustrated in FIG. 3. In step 1004, external detector devices 310 are positioned in a predetermined arrangement on a surface of the subject's body 50. The predetermined arrangement on the subject's body 50 can be based on bony landmarks of the subject's anatomy.

In step 1006, the signal system 320 is inserted into the feeding tube 310 such that the coil 322 is disposed at the distal end 312 of the feeding tube 310, and then the feeding tube 310 can be inserted into the subject, e.g., through the subject's nose or mouth. Then, in step 1080, the in-scale display device 100 can be positioned in a predetermined arrangement over the surface of the subject's body, as shown in FIG. 1, such that the surface area 122 of the display 120 is positioned above the distal end 312 of the feeding tube 10.

In step 1010, the processor 132 sends at least one drive signal to generate a signal 226 with the signal generator 222, e.g., coil, and the signal generators 380 of each external detector device 310. Once the feeding tube 310 has been inserted, a signal, e.g., the voltage of the current induced in the electromagnetic receiver 140 by an electromagnetic field 226, is detected in step 1012. In step 1014, the signal, e.g., the voltage of the induced current of the electromagnetic receiver 140, can be used by the processor 132 to determine the position and orientation of the coil 322 of the signal generator system 320 of the invasive medical device system 200 relative to the external detector devices 310 and the surface area 122 of the display device 100.

In step 1016, the processor 132 then causes the electronic display 120 to display the position and orientation of the signal generator 322 within the distal end of the feeding tube 310 relative to the receiver 140 of the display device 100 in a superior/inferior direction and/or a medial/lateral direction relative to the subject 50. The processor 132 can also cause the electronic display 120 to display reference images of anatomical landmarks of the subject's external or internal anatomy. The images displayed can be in the form of at least one reference image that is in-scale with the size and position of the subject's body 50. Although the above embodiments relate to positioning an end of a feeding tube catheter, it should be appreciated that the display device of the medical device position guidance system is operable to assist in the placement of any medical device or invasive component into a mammal in the course of stent placement, ablation, blockage removal, heat treatment, surgical procedure, fluid delivery or any other suitable invasive procedure. It should be appreciated that any type of catheter may be used for any of the medical procedures described above. It should also be appreciated that any suitable invasive medical device can be used in place of a catheter. Further, it should be appreciated that the in-scale display device can be used to display a reference image of any other suitable subject outside the medical field when a sufficient signal generator is used with the in-scale display device.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A display device comprising:
   at least one electronic display screen having a surface area;
   at least one signal receiver configured to detect a signal generated by a signal generator;
   a processor; and
   a memory device storing pre-defined anthropomorphic relationships between at least one known external anatomical landmark and the approximate three-dimensional location and size of at least one internal anatomical structure based on the at least one pre-defined anthropomorphic relationship,
   the memory device storing instructions which, when executed by the processor, cause the processor to
   (i) display a first reference image of a subject's anatomy on the electronic display screen,
   (ii) detect the signal generated by the signal generator,
   (iii) determine the distance between the at least one signal receiver and the signal generator,
   (iv) determine the size, position and/or orientation of the signal receiver relative to the signal generator in-scale with the patient's anatomy based on the pre-defined anthropomorphic relationships stored in the memory device, and
   (v) cause the display device to display at least one second reference image on the electronic display screen representing the size, position and/or orientation of the signal receiver relative to the signal generator, wherein the at least one second reference image is in-scale with the signal generator and in-scale with the first reference image such that the actual size of the size, position and/or orientation of the signal receiver relative to the signal generator and the patient's anatomy is displayed in real time.

2. The display device of claim 1, wherein the at least one signal receiver comprises an electromagnetic receiver having at least one wire coil, further wherein the at least one signal receiver detects an electromagnetic field generated by the signal generator by measuring a voltage of a current induced in the at least one wire coil by the electromagnetic field.

3. The display device of claim 1, wherein the electronic display screen is configured to be placed within a target area over a target area of the subject.

4. The display device of claim 3, wherein the at least one reference image is configured to represent the size, position and/or orientation of the signal receiver relative to the signal generator based on the location of the signal receiver within the target area relative to the signal generator.

5. The display device of claim 3, wherein when the electronic display screen moves from a first point within the target area to a second point within the target area, the at least one reference image moves to display the location of the at least one signal receiver at the second point within the target area.

6. The display device of claim 1, wherein the electronic display screen is configured to be movable in relation to a surface of the subject's body.

7. The display device of claim 1, wherein the display device is integrated into a tablet computer or mobile device.

8. The display device of claim 1, wherein the electronic display screen is configured to display movement of the signal generator in the superior/inferior and/or lateral/medial directions of the subject's body when the electronic display screen is placed over an anterior surface of the subject's body.

9. The display device of claim 1, wherein the electronic display screen is configured to display movement of the signal generator in the superior/inferior and/or dorsal/ventral directions of the subject's body when the electronic display screen is placed over a lateral surface of the subject's body.

10. A medical device position guidance system comprising:
an invasive medical device assembly;
at least one signal generator/receiver configured to generate a signal; and
a display device, the display device being positionable over a surface of a subject;
the invasive medical device assembly including:
a sensor configured to detect a signal generated by the at least one signal generator/receiver; and
an invasive medical device configured to support the sensor, the invasive medical device having an end portion configured to be inserted into the subject, and wherein the invasive medical device assembly is operatively coupled to the display device;
the display device including:
at least one electronic display screen having a screen surface area;
a signal receiver configured to detect a signal by the at least one signal generator/receiver;
a processor; and
a memory device storing pre-defined anthropomorphic relationships between at least one known external anatomical landmark and the approximate three-dimensional location and size of at least one internal anatomical structure based on the at least one pre-defined anthropomorphic relationship,
the memory device storing instructions which, when executed by the processor, cause the processor to
(i) display a first reference image of a subject's anatomy on the electronic display screen,
(ii) detect the signal generated by the signal generator/receiver via the sensor of the medical device and the signal receiver of the display device,
(iii) determine the distance between the at least one signal generator/receiver and the sensor of the medical device,
(iv) determine the distance between the at least one signal generator/receiver and the signal receiver of the display device,
(v) determine the size, position and/or orientation of the signal receiver relative to the signal generator in-scale with the patient's body based on the pre-defined anthropomorphic relationships stored in the memory device, and
(vi) cause the display device to display on the at least one electronic display screen at least one second reference image of the size, position and/or orientation of the sensor of the medical device in relation to the position of the at least one electronic display screen, wherein the at least one second reference image is configured to be in-scale with the subject's body and in-scale with the first reference image such that the actual size of the size, position and/or orientation of the sensor of the medical device relative to the electronic display screen and the patient's body is displayed in real time.

11. The medical device position guidance system of claim 10, wherein the at least one signal generator/receiver comprises three signal generator/receivers configured to triangulate a shape and size of the subject's anatomy.

12. The medical device position guidance system of claim 10, wherein the at least one sensor of the medical device comprises an electromagnetic field sensor having at least one wire coil, further wherein the at least one sensor detects a signal generated by the at least one signal generator/receiver by measuring a voltage of a current induced in the at least one wire coil by the electromagnetic field.

13. The medical device position guidance system of claim 10, wherein the electronic display screen is configured to be placed over a target area of the subject.

14. The medical device position guidance system of claim 13, wherein the display device displays the at least one reference image when the sensor of the medical device is positioned beneath the screen surface area when the electronic display screen is placed over the target area of the subject.

15. The medical device position guidance system of claim 10, wherein the electronic display screen is configured to be movable in relation to a surface of the subject's body.

16. The medical device position guidance system of claim 10, wherein when the electronic display screen moves in relation to a surface of the subject's body, the at least one reference image changes to display the location of the at least one sensor of the medical device beneath the moved surface area of the at least one electronic display screen.

17. The medical device position guidance system of claim 10, wherein the display device is integrated into a tablet computer.

18. A method of guiding the positioning of an invasive medical device, the method comprising the steps of:
providing the medical device position guidance system of claim 10;
inserting the invasive medical device into the subject's body;
positioning the screen surface area of the display device over a target area of the subject's body in a predetermined arrangement such that the at least one signal receiver of the display device is in a predetermined position;
determining the position of the at least one sensor of the medical device with respect to the at least one signal generator/receiver;
determining the position of the at least one signal receiver of the display device with respect to the at least one signal generator/receiver; and
displaying the position of the at least one sensor of the medical device on the at least one electronic display screen when the at least one sensor of the medical device is positioned within the target area of the subject's body.

19. The method of claim 18, further comprising a step of positioning the at least one signal generator/receiver on a surface of the subject.

20. The method of claim 19, further comprising a step of placing the display device over a surface of the subject after the step of positioning the at least one signal generator/receiver on a surface of the subject.

21. The method of claim 18, further comprising a step of moving the screen surface area of the display device in relation to the subject, wherein the at least one reference image changes to display the location of the at least one sensor of the medical device below the screen surface area of the at least one electronic display screen as the at least one electronic display screen moves.

* * * * *